(12) United States Patent
Uckelmann

(10) Patent No.: US 9,149,989 B2
(45) Date of Patent: Oct. 6, 2015

(54) PARTICLE SIZE INFLUENCING LAYER-BY-LAYER MANUFACTURING METHOD

(75) Inventor: Ingo Uckelmann, Bremen (DE)

(73) Assignee: BEGO MEDICAL GMBH, Bremen (DE)

(*) Notice: Subject to any disclaimer, the term of this patent is extended or adjusted under 35 U.S.C. 154(b) by 1190 days.

(21) Appl. No.: 12/090,630

(22) PCT Filed: Oct. 19, 2006

(86) PCT No.: PCT/EP2006/010090
§ 371 (c)(1),
(2), (4) Date: Aug. 7, 2008

(87) PCT Pub. No.: WO2007/045471
PCT Pub. Date: Apr. 26, 2007

(65) Prior Publication Data
US 2009/0176007 A1    Jul. 9, 2009

(30) Foreign Application Priority Data
Oct. 20, 2005  (DE) .......................... 10 2005 050 665

(51) Int. Cl.
*B29C 35/08* (2006.01)
*B29C 67/00* (2006.01)
(Continued)

(52) U.S. Cl.
CPC ......... *B29C 67/0092* (2013.01); *A61C 13/0018* (2013.01); *B22F 3/1055* (2013.01); *B29C 67/0077* (2013.01); *B22F 2003/1057* (2013.01); *B22F 2998/00* (2013.01)

(58) Field of Classification Search
USPC ............... 264/1.7, 510, 297.4, 642, 471, 473, 264/476, 477, 481, 482, 112, 171.1
See application file for complete search history.

(56) References Cited

U.S. PATENT DOCUMENTS 5,147,587 A * 9/1992 Marcus et al. ................ 264/434
5,182,170 A * 1/1993 Marcus et al. ................ 264/497
(Continued)

FOREIGN PATENT DOCUMENTS

CA  2427087   3/2003
DE  43 09 524  11/1993 .............. B29C 39/42
(Continued)

OTHER PUBLICATIONS

*International Search Report and the Written Opinion of the International Searching Authority*, International Application No. PCT/EP2006/010090, Feb. 20, 2007, 15 Pages.
(Continued)

*Primary Examiner* — Stella Yi
(74) *Attorney, Agent, or Firm* — Kilpatrick Townsend and Stockton LLP

(57) ABSTRACT

The invention concerns a process for the layerwise production of a product comprising the steps of applying a layer of a hardenable material, wherein for example the process parameters of layer thickness and layer material are adjustable, selectively hardening predetermined regions of the applied layer on the basis of the geometrical data of the product, wherein for example the process parameters for the nature and level of the energy input are adjustable, repeating those steps until the geometry of the product has been produced in the form of hardened material, and finally removing the non-hardened material. Known processes suffer from the disadvantage that they do not afford variability in regard to the local properties of the product. The invention remedies that disadvantage insofar as at least one process parameter is altered during the production procedure in order to influence the grain size in a first region of the product in relation to a second region of the product.

12 Claims, 1 Drawing Sheet

(51) Int. Cl.
*A61C 13/00* (2006.01)
*B22F 3/105* (2006.01)

(56) References Cited

U.S. PATENT DOCUMENTS

2002/0145213 A1* 10/2002 Liu et al. .................. 264/40.1
2003/0029212 A1* 2/2003 Im ................................ 72/54
2003/0206820 A1* 11/2003 Keicher et al. ................ 419/9

FOREIGN PATENT DOCUMENTS

| DE | 195 38 257 | 4/1996 | ............. B29C 39/42 |
| DE | 103 20 085 | 2/2004 | ............. B22F 3/105 |
| EP | 1 358 855 | 11/2003 | ............. A61C 13/00 |
| WO | WO 2004/089851 | 10/2004 | ............. C04B 35/64 |

OTHER PUBLICATIONS

The International Bureau of WIPO, International Preliminary Report on Patentability (Including the Written Opinion of the International Searching Authority)—Appl. No. PCT/EP2006/010090, dated Apr. 22, 2008 (8 pages).

The International Searching Authority, English Translation of The Written Opinion of the International Searching Authority—Appl. No. PCT/EP2006/010090, dated Feb. 26, 2007 (8 pages).

The Office Communication received in related CA Application No. 2,625,556 dated Jul. 26, 2012.

* cited by examiner

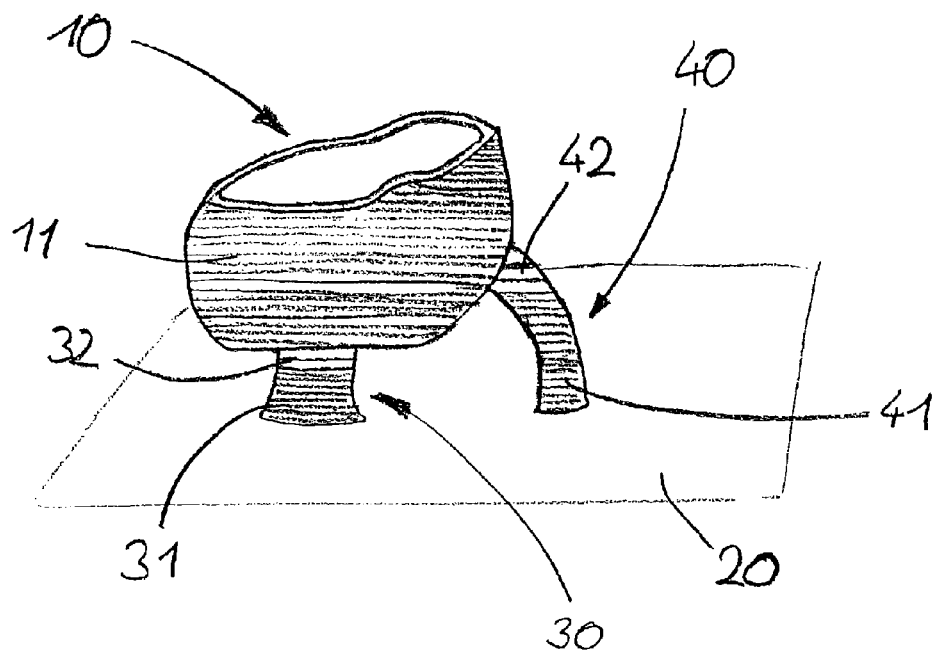

PARTICLE SIZE INFLUENCING LAYER-BY-LAYER MANUFACTURING METHOD

The invention concerns a process for the layerwise production of a product comprising the steps:

a. applying a layer of a hardenable material, wherein for example the process parameters of layer thickness and layer material are adjustable, b. selectively hardening predetermined regions of the applied layer on the basis of the geometrical data of the product, wherein for example the process parameters for the nature and level of the energy input are adjustable, c. repeating steps a) and b) until the geometry of the product has been produced in the form of hardened material, and d. removing the non-hardened material.

A further aspect of the invention is an apparatus for carrying out such a process and the use of the process and the apparatus for the production of dental products.

Processes of the kind set forth in the opening part of this specification are employed in many uses in order to produce geometrically complex products at the lowest possible level of complication and expenditure in terms of manufacturing preparation, and in the shortest possible time. A typical example of use is what is referred to as 'rapid prototyping' in which a product model is produced directly from product geometry data describing the three-dimensional form of the product, which product model can serve for visual examination and testing.

Processes of the kind set forth in the opening part of this specification can be carried out for example with a material in powder form or which is capable of flow in another fashion and which can be hardened by a chemical crosslinking reaction or a physical combining operation, for example fusing or sintering, and in that way can produce a three-dimensional structure which is capable of bearing a load. In other situations of use it is also possible to employ a fluid hardenable material which for example can be selectively hardened by photopolymerisation by means of a laser beam.

A usual process of the kind set forth in the opening part of this specification provides that the pourable or castable material is applied to a plate in a thin layer and then given regions of that layer are hardened by a laser beam being passed over that region and thus causing hardening, for example fusing, sintering or photopolymerisation.

Subsequently a second thin layer is applied to the previously applied thin layer, for example by a thin powder layer being additionally applied or by the plate being lowered by a given small distance into a bath of the liquid hardenable material. Once again certain regions of that second thin layer are selectively hardened. Those process steps are repeated a plurality of times in succession until the product has been produced in that way in the form of a layerwise hardened model.

A process of the above-described kind for the production of products by freeform laser sintering is described in EP 1 358 855. A development of the process with dual exposure is described in EP 1 568 472.

Processes of the above-described kind are suitable for the production of mechanically loadable products. Particularly in the production of metallic products, satisfactory mechanical properties can be achieved in the product, using the process set forth in the opening part of this specification.

It has been found however that the production process referred to in the opening part of this specification can be still further improved, in particular for highly loaded products involving complex geometries. Thus, particularly in relation to such products, overstressing of the material is occasionally observed at exposed or highly loaded locations. That can result in reduced load-bearing capacity on the part of the product or even local failure of the product. Furthermore, for certain regions of the material in the product itself or in manufacturing assistance regions, for example supports, it is often desirable to reduce the strength of the material in order to afford desired-rupture locations. That cannot be reproducibly achieved with the previously known processes.

The object of the invention is to provide a process with which products involving complex geometries and strength levels of variable nature, in particular with regions which locally can bear a high loading, can be economically produced in small numbers, in particular as a single-item manufacture.

According to the invention that object is attained by a process of the kind set forth in the opening part of this specification, in which at least one process parameter is altered during the production procedure in order to influence the grain size in a first region of the product in relation to a second region of the product.

The invention is based on the decisive realisation that the locally inadequate material properties of products which were produced with the process set forth in the opening part of this specification are frequently to be attributed to the fact that an unfavourable grain size is produced by virtue of locally limited influences in a given region or a plurality of given regions of the product in production of the product. The result of this is that the product does not have the desired material properties at the corresponding locations but is characterised by other undesirable material properties which do not fulfil the material properties which are desired in the corresponding region.

Building on that realisation the invention provides that one or more process parameters is or are so altered during the production operation that the grain size is influenced in such a way that a desired size is achieved in the corresponding region. In that way it is possible for example to achieve a homogeneous material structure with uniform grain size in all regions or it is possible to form given regions which are of a different grain size in relation to other regions.

In this connection the reference to grain size is intended to denote in particular the size of the crystals of a metallic product, which is usually ascertained microscopically on the basis of etched ground sections.

It is preferable for the at least one process parameter to be altered in dependence on the geometrical data of the product. It has been found that an unfavourable configuration in respect of the grain size or grain boundary surface size frequently depends on the geometrical configuration of the product. Thus such an unwanted grain size configuration is frequently observed in the region of surfaces, exposed projections or the like on the product. The above-mentioned development of the process makes it possible for one or more process parameters to be altered targetedly and specifically in such regions of the product in order to counteract an unwanted grain size alteration which is observed or to be expected. In that way it is possible for example to provide that the product is of uniform grain size in two or more regions which would involve different grain sizes by virtue of different processing conditions, for example different levels of heat conduction, even if the process parameters were kept constant throughout the entire processing operation, insofar as one or more process parameters are deliberately altered. In that respect that alteration can be set specifically in locationally resolved relationship on the basis of the geometrical data of the product and in that way can be automatically controlled.

Furthermore that development of the process can be used to deliberately and targetedly alter given geometrical regions of the product in respect of the grain size thereof, for example to achieve a different grain size in the region of the surfaces, from the grain size in the internal region of the product. Thus for example it is possible to achieve a particularly high level of hardness, strength, particularly advantageous workability or particularly advantageous capacity for glueing of the product in the surface region.

It is further advantageous if the material is applied with a different layer thickness in a first region of the product from that in a second region in order to influence the grain size in the first region in relation to the second region. It has been found that the layer thickness, that is to say the height to which a single layer of the hardenable material is applied, has a substantial influence on grain size. The relationship is such that, upon an increase in the layer thickness, an increase in the size of the grains is achieved in the region of that layer. That relationship is used in accordance with this development in order to influence the grain size by a variation in the process parameter of the layer thickness, that is to say, to reduce the layer thickness if the grain size is to be reduced and vice-versa. That allows the grain size to be individually influenced. Thus a single layer can be applied on the one hand with a uniform layer thickness. Developments in the process can also be implemented in which a single layer is applied in two or more different layer thicknesses at different locations of the layer. As an alternative thereto a region which is to be hardened can be hardened only after multiple layer application in order in that way to achieve an increased layer thickness in that region and at the same time to make it possible for other regions which are to be hardened to be hardened previously of a smaller layer thickness.

It is further preferred if hardening of the material is achieved by means of a laser or electron beam which is passed over the regions to be hardened and the intensity of the radiation is altered in a first region of the product in relation to a second region in order to influence the grain size in the first region in relation to the second region. Hardening with a laser or electron beam permits highly variable control of the process and allows the production of geometrically precise products. The intensity of the radiation has been found to be an important factor influencing the grain size and a variation in the parameter of radiation intensity therefore makes it possible to influence the grain size. That development of the process enjoys the decisive advantage that the intensity of the radiation can be altered in a highly resolved fashion in respect of time and place and that therefore permits highly precise implementation of the procedure with appropriately differentiated and precise influencing of the grain size.

It is particularly preferred in that respect if the intensity of the radiation is altered by the radiation source power, the diameter of the beam at the focus and/or the speed of displacement as between the beam and the material to be hardened being altered. The diameter of the beam at the focus can be influenced easily and quickly by a lens system having a variable focal length. The speed of displacement between the beam and the material to be hardened can be produced either by deflection of the beam, for example by way of mirror or prism elements, or by means of a motor drive which moves the material to be hardened relative to the beam or the beam unit relative to the material to be hardened. Those possible options also allow a simple and readily controllable variation in the speed of displacement. Finally, the radiation source power can be particularly rapidly altered for example by an increased feed of energy to the radiation source or by operatively cutting beam splitters into and out of the beam and is therefore particularly suitable for influencing grain size. An increase in the diameter of the beam in the processing region, in particular at the focus, a reduction in the radiation source power and/or an increase in the speed of displacement cause in that case a reduction in the intensity of the radiation and vice-versa.

It is particularly preferred if in a first region of the product with a higher degree of heat conduction than in a second region, in particular
- in a first region involving a greater wall thickness of the product and/or
- in a first region which is in contact with a plate on which the component is built up and/or
- in a first region of an overhang of the product at least one process parameter is altered in relation to the second region in order to influence the grain size.

In that respect it is particularly preferred if the intensity of the radiation and/or the layer thickness is increased in the first region in order to keep the grain size in the first region constant in relation to the second region.

It has been found that an unwanted change in the grain size often occurs in those regions in which there is a modified heat conduction in relation to other regions. Such a modified heat conduction can be caused for example by geometrical factors, it can be caused by an alteration in the material properties or it can be caused as a consequence of the sequence in which the regions to be hardened are processed. A change caused thereby in the grain size or grain boundary surfaces is often unwanted and leads to disadvantageous product properties. In particular regions involving a greater wall thickness, regions which are in contact with the base plate and regions in which the product has an overhang, for example a projection or the like, have been found to be particularly critical in regard to grain size.

The development provides that one or more process parameters is altered in the regions involving altered heat conduction in order to compensate for the unwanted modification in size or in addition to bring about a change in size in an intended fashion. In that way it is possible to achieve a homogeneous size for the grains in the entire product or it is possible to provide that an advantageous grain size is produced in the regions involving altered heat conduction, which often coincide with geometrically exposed and therefore mechanically particularly stressed regions of the product, in order to produce desired advantageous material properties in those regions. The process according to the invention is particularly suitable for achieving constancy in respect of grain size in those regions, by a procedure whereby one or more process parameters are altered in those regions in relation to other regions during the processing operation.

In principle the process according to the invention can advantageously be used to alter one or more process parameters during the production operation and in that way to keep the grain size approximately constant in all regions of the product.

In certain uses however it is particularly preferred if the at least one process parameter is altered to alter the grain size in a first region of the product in relation to the second region. It is possible in that way to produce a grain size which is adapted to the loadings of the individual regions and in that fashion it is possible to achieve an adapted material property for each region of the product.

It is particularly preferred if the layer thickness is increased and/or the intensity of the radiation is increased in the first region in order to increase the grain size in a first region of the product in relation to the second region. It has been found that an increase in the size of the grains occurs for a series of conventional hardenable materials if the materials are applied with an increased layer thickness and that layer thickness is then selectively hardened. In that case a change in the layer thickness can be effected in all regions of the layer or in only individual regions of the layer.

In the above-described processes involving an alteration in the process parameter consisting of the intensity of the radiation it is particularly preferred if the intensity of the radiation is increased by the radiation source power being increased and/or the diameter of the beam at the focus and/or the speed of displacement between the beam and the material to be hardened being reduced in order to increase the grain size in a first region of the product in relation to the second region. An alteration in those specific process parameters, in isolation or in combination, leads to the desired increase in the intensity of the radiation.

It is further preferred if the at least one process parameter is altered in order to reduce the size of at least one flaw. In this connection the term grain size is also intended to denote a flaw size. A flaw can consist of an air-filled space within a component or a locally defined region which contains contamination or soiling, alloying impurity or the like. Such flaws usually influence the material properties and that influence generally causes the material properties to be worsened, such worsening being all the more pronounced, the larger the flaw is. It is therefore desirable to keep the size of the flaw below a given maximum size if a predetermined target strength is wanted on the part of the material. Conversely it may be desirable to provide flaws of a given order of magnitude or thereabove in order to ensure that a desired material failure occurs at a predetermined reference loading.

It has been found that it is possible to influence the flaw size by altering one or more process parameters and consequently the flaw size can be set below or above a given limit by one or more process parameters being specifically altered.

In that respect it is particularly preferred if in the first region the layer thickness is reduced and/or the radiation intensity or the speed of displacement is increased in order in the first region to prevent flaws consisting of insoluble melting impurities which occur in the molten material or during the cooling operation combining to form larger flaws. Insoluble impurities in the molten material typically already occur in the material when it is in the liquid molten state or during the cooling operation and, if mobility of that flaw is made possible, can combine together and in that way form larger flaws. That is often undesirable as that reduces the load-bearing capability of the component produced and, in accordance with the development of the invention, the mobility of the flaw is not made possible or is made possible only for a short time by the parameters being selected as described hereinbefore.

Another development in relation thereto of the process according to the invention provides that in the first region the layer thickness is increased and/or the radiation intensity or the speed of displacement is reduced in order in the first region to prevent flaws consisting of soluble melting impurities combining to form larger flaws. Soluble impurities in the molten material can be distributed over a relatively large region of the material by a prolongation of the liquid molten state, whereby the influence of the impurity is reduced by the concentration thereof being reduced. That prolongation of the liquid molten state can be achieved by the parameters being varied, as described hereinbefore.

It will be apparent from the two aforementioned developed variants of the process that a parameter variation has to be effected in material-specific relationship in dependence on the nature of the impurity in order to achieve the desired result in regard to the size of the flaws. In that respect preceding analysis of the nature and manner of the molten material impurity is advantageous. In addition, using analytical values or empirically determined values, it is possible to effect a parameter variation in given regions of the component in which experience has shown that certain kinds of molten material impurity—soluble or insoluble—occur.

A further aspect of the invention is an apparatus for the layerwise production of a product, comprising:
  a. means for applying a layer of a hardenable material, wherein by way of example the process parameters of layer thickness and layer material are adjustable,
  b. means for selectively hardening predetermined regions of the applied layer on the basis of the geometrical data of the product, and
  c. control means for adjusting the process parameters for the nature and level of the energy input,
wherein the control means are adapted to alter at least one process parameter during the production operation in order to influence the grain size in a first region of the product in relation to a second region of the product. The apparatus according to the invention is designed in particular to carry out the process according to the invention. In terms of the details of the parts of the apparatus corresponding to the individual process steps, the actions thereof and the advantages thereof, attention is directed to the preceding description.

The apparatus according to the invention can be further developed in accordance with the features set forth in the claims. In regard to those developments, in terms of the details, mode of operation and advantages attention is directed to the developments of the processes which correspond to the apparatus features and which have been described hereinbefore.

The apparatus according to the invention is suitable in particular for use in the production of dental products, in particular for partial or complete tooth prosthesis. Such a tooth prosthesis can completely replace a missing, diseased or damaged tooth or can be fitted in the region of damaged or diseased locations of a tooth to sound parts of the tooth and can thereby restore the tooth again from a functional and an aesthetic point of view. The apparatus according to the invention is particularly suitable for the production of such a tooth prosthesis as on the one hand highly individual manufacture can be effected on the basis of geometry data ascertained for example with an image acquisition system and on the other hand a grain size which is matched to the stresses on the tooth prosthesis can be set. Thus for example particularly advantageous adhesion of the tooth prosthesis to existing remaining pieces of a tooth or teeth or particularly desirable integration of the tooth prosthesis into the jawbone can be achieved by the surface being formed with a grain size and a grain boundary surface size which is advantageous in that respect. Furthermore the surfaces which are stressed by friction during the mastication operation can be provided with a grain size which is particularly insensitive in relation to such frictional influences. Finally the interior of the tooth prosthesis can be provided with a grain size which is particularly suitable for transmitting the mechanical mastication forces within the tooth prosthesis portion. Thus the process according to the invention makes it possible to set the grain sizes in a range of between 0.5 and 5 µm.

A further aspect of the invention is a process of the above-described kind for the production of dental products, in particular partial or complete tooth prosthesis. In regard to the advantages of that development of the process attention is directed to the foregoing description of the corresponding use of the apparatus.

An embodiment which is preferred at the present time is described by way of example with reference to the accompanying FIGURE which shows a dental product 10 built up on a base plate 20.

The dental product 10 is connected to the base plate 20 by way of a build-up leg 30 and a support 40 and is thereby spaced from the base plate 20. The dental product is produced from a plurality of layers 11 which are successively applied and hardened.

Before the dental product itself is produced by layerwise hardening of the starting material, the build-up leg 30 is also produced by layerwise hardening. In that case, in the region which adjoins the base plate, operation is also effected with very thin layers 31. In the transitional region between the build-up leg and the dental product however the layer height of the layers 32 is trebled in comparison with those thin layers, whereby a greater grain size is achieved in that region.

In that way, a desired-rupture location is formed in the transitional region by the modification in grain size, which allows the build-up leg to be more easily separated from the dental product without that giving rise to the risk of the dental product being damaged in the separation operation or relatively large parts of the build-up leg remaining on the dental product, which would require complicated and expensive post-working operations.

The dental product 10 is further supported laterally by the support 40 in order to counteract the forces which occur in the layer application procedure and to prevent unwanted geometrical distortion of the dental product. A plurality of such supports 40 are often required in order to sufficiently mechanically secure the dental product or filigree constituents parts of the dental product.

The support 40 is also built up in the region 41 adjoining the base plate 20, with a large number of thin layers. In the transitional region 42 in which the support 40 adjoins the dental product 10 and blends into the dental product 10, the layer thickness is trebled, as also in the case of the connecting leg 30, whereby an increased grain size is produced in that region. In that way, a desired-rupture location is produced by the increase in grain size and easy separation of the support 40 from the dental product 10 without any risk is possible.

What is claimed is:

1. A process for layerwise production of a metallic product comprising the steps of:
   a. applying a layer of non-hardened metallic material, the material capable of being hardened, wherein process parameters of layer thickness and layer material are adjustable;
   b. selectively hardening predetermined regions of the applied layer of the metallic material on the basis of the geometrical data of the product, wherein the process parameters for the nature and level of the energy input are adjustable;
   c. repeating steps a) and b) until the geometry of the product has been produced in the form of hardened material; and
   d. removing a remaining non-hardened metallic material from the regions that were not selectively hardened,
   wherein at least one process parameter is adjusted during the production process in order to influence a crystal size of a finished product produced in a first region of the product in relation to a second region of the product as the predetermined regions of the applied layer are selectively hardened,
   wherein the non-hardened metallic material is applied with a different layer thickness in the first region of the product from that in the second region of the product in order to influence the crystal size in the first region in relation to the second region of the product.

2. A process according to claim 1 wherein the at least one process parameter is adjusted in dependence on the geometrical data of the product.

3. A process according to claim 1 wherein hardening of the material is achieved by means of a laser or electron beam which is passed over the regions to be hardened and an intensity of radiation is adjusted in the first region of the product in relation to the second region of the product in order to influence the crystal size in the first region in relation to the second region of the product.

4. A process according to claim 3 wherein the intensity of the radiation is adjusted by a radiation source power and a diameter of the electron beam in the processing region wherein a focus and/or a speed of a displacement between the beam and the material to be hardened is adjusted.

5. A process according to claim 4 wherein the intensity of the radiation is increased by increasing the radiation source power and/or reducing the diameter of the beam in the processing region at a focus region and/or the speed of displacement between the beam and the material to be hardened in order to influence the crystal size in the first region of the product in relation to the second region of the product.

6. A process according to claim 3 further wherein the first region of the product-has a higher degree of heat conduction than the second region of the product,
   the first region involving a greater wall thickness of the product and/or;
   the first region is in contact with a plate on which the product is built up and/or;
   the first region of an overhang of the product includes adjusting the at least one process parameter in relation to the second region by adjusting an intensity of radiation and/or increasing the layer thickness in the first region to influence the crystal size.

7. A process for layerwise production of a metallic product comprising the steps of:
   a. applying a layer of non-hardened metallic material, the material capable of being hardened, wherein process parameters of layer thickness and layer material are adjustable;
   b. selectively hardening predetermined regions of the applied layer of the metallic material on the basis of the geometrical data of the product, wherein the process parameters for the nature and level of the energy input are adjustable;
   c. repeating steps a) and b) until the geometry of the product has been produced in the form of hardened material; and
   d. removing a remaining non-hardened metallic material from the regions that were not selectively hardened,
   wherein at least one process parameter is adjusted during the production process in order to influence a crystal size of a finished product produced in a first region of the product in relation to a second region of the product as the predetermined regions of the applied layer are selectively hardened,
   wherein the at least one process parameter is adjusted on the basis of the geometrical data of the product in the first region of the product in relation to the second region of the product in order to keep the crystal size in the first region of the product approximately constant in relation to the second region of the product.

8. A process according to claim 1 wherein the at least one process parameter is adjusted to alter the crystal size or a crystal boundary surface in the first region of the product in relation to the second region of the product.

9. A process for layerwise production of a metallic product comprising the steps of:
   a. applying a layer of non-hardened metallic material, the material capable of being hardened, wherein process parameters of layer thickness and layer material are adjustable;
   b. selectively hardening predetermined regions of the applied layer of the metallic material on the basis of the geometrical data of the product, wherein the process parameters for the nature and level of the energy input are adjustable;
   c. repeating steps a) and b) until the geometry of the product has been produced in the form of hardened material; and
   d. removing a remaining non-hardened metallic material from the regions that were not selectively hardened,
   wherein the at least one process parameter is adjusted to alter the crystal size or a crystal boundary surface in the first region of the product in relation to the second region of the product, and
   wherein at least one process parameter is adjusted during the production process in order to influence a crystal size of a finished product produced in a first region of the product in relation to a second region of the product as the predetermined regions of the applied layer are selectively hardened,
   wherein the layer thickness is increased and/or an intensity of radiation is increased in the first region in order to increase the crystal size or the crystal boundary surface in the first region of the product in relation to the second region of the product.

10. A process according to claim 1 wherein the at least one process parameter is adjusted in order to reduce a size of at least one flaw.

11. A process according to claim 10 wherein in the first region of the product, the layer thickness is reduced and/or an intensity of radiation or the speed of displacement is increased in order to prevent flaws in the first region, the flaws including insoluble melting impurities which occur in the molten material or during the cooling operation combining to form larger flaws.

12. A process according to claim 10 wherein in the first region of the product, the layer thickness is increased and/or the intensity of radiation or the speed of displacement is reduced in order to prevent flaws in the first region, the flaws including soluble melting impurities combining to form larger flaws.

* * * * *

UNITED STATES PATENT AND TRADEMARK OFFICE
CERTIFICATE OF CORRECTION

PATENT NO. : 9,149,989 B2
APPLICATION NO. : 12/090630
DATED : October 6, 2015
INVENTOR(S) : Uckelmann It is certified that error appears in the above-identified patent and that said Letters Patent is hereby corrected as shown below:

In the claims

Column 8, Claim 6, Line 29

Replace "product-has" with "product has"

Signed and Sealed this
Twelfth Day of April, 2016

Michelle K. Lee
*Director of the United States Patent and Trademark Office*